United States Patent [19]

Anderegg et al.

[11] Patent Number: 5,159,189

[45] Date of Patent: Oct. 27, 1992

[54] METHOD AND APPARATUS FOR MEASURING THE NATURAL COLOR OF SLIVERS

[75] Inventors: Peter Anderegg; Robert Moser, both of Winterthur; Jurg Faas, Dinhard, all of Switzerland

[73] Assignee: Maschinenfabrik Rieter AG, Winterthur, Switzerland

[21] Appl. No.: 668,030

[22] Filed: Mar. 12, 1991

[30] Foreign Application Priority Data

Mar. 12, 1990 [CH] Switzerland ............. 00786/90
Apr. 19, 1990 [CH] Switzerland ............. 01319/90

[51] Int. Cl.⁵ .................... G01N 21/00; G01J 3/50
[52] U.S. Cl. .................... 250/226; 356/238; 356/429
[58] Field of Search .............. 250/226, 548, 571; 356/238, 429, 430, 431

[56] References Cited

U.S. PATENT DOCUMENTS

| | | |
|---|---|---|
| 3,496,366 | 2/1970 | Hunziker et al. |
| 3,524,988 | 8/1970 | Gaither ............. 356/238 |
| 3,573,476 | 4/1971 | Falcoff et al. ............. 356/425 |
| 3,641,626 | 2/1972 | McGill . |
| 3,986,778 | 10/1976 | Mathisen et al. ............. 356/244 |
| 4,022,534 | 5/1977 | Kishner ............. 356/446 |
| 4,194,840 | 3/1980 | Lucas et al. . |
| 4,284,356 | 8/1981 | Heilman ............. 356/429 |
| 4,346,997 | 8/1982 | Willis . |
| 4,490,618 | 12/1984 | Ciclo ............. 356/429 |
| 4,758,968 | 7/1988 | Lord . |
| 4,990,793 | 2/1991 | Bognigk et al. ............. 356/238 |

FOREIGN PATENT DOCUMENTS

| | | |
|---|---|---|
| 637961 | 3/1964 | Belgium . |
| 3327966 | 2/1985 | Fed. Rep. of Germany . |
| 6700295 | 3/1967 | Netherlands . |

OTHER PUBLICATIONS

"Problems Associated with Color Measurements, Reflectance and Transmittance", Hoban, R. F., Textile Chemist and Colorist, vol. 13, No. 5, pp. 112-114, May 1981.

Primary Examiner—Bruce C. Anderson
Attorney, Agent, or Firm—Sandler, Greenblum & Bernstein

[57] ABSTRACT

A method and apparatus for in-line color measurement of continuously moving fiber material, during a fiber material process, by using a color measuring device. The moving fiber material is compressed at a processing position. At the processing position, the fiber material is illuminated by a light probe, thereby defining a measuring position. The light reflected from the fiber material is detected and evaluated to thereby obtain a color measurement of the advancing fiber material.

39 Claims, 4 Drawing Sheets

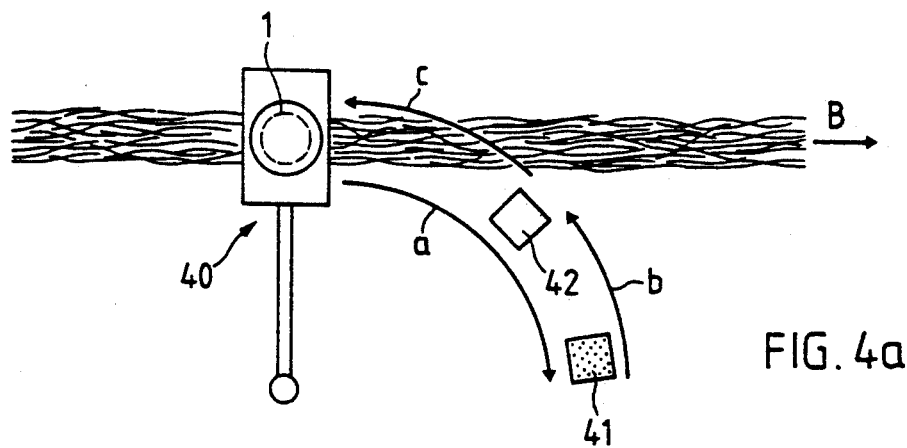
FIG. 4a
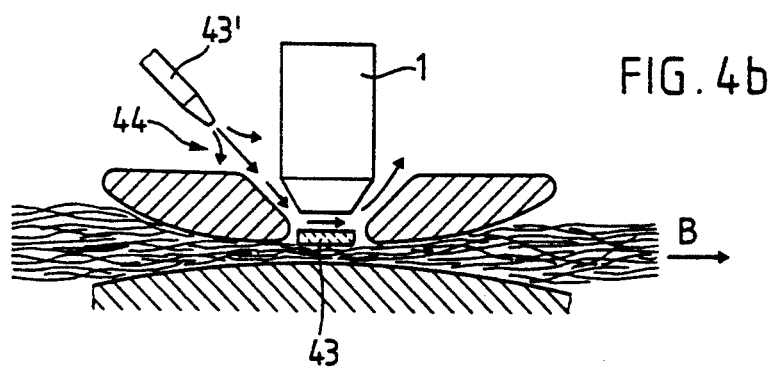
FIG. 4b
FIG. 4c
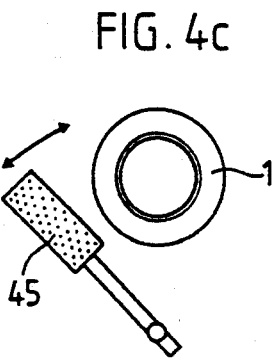
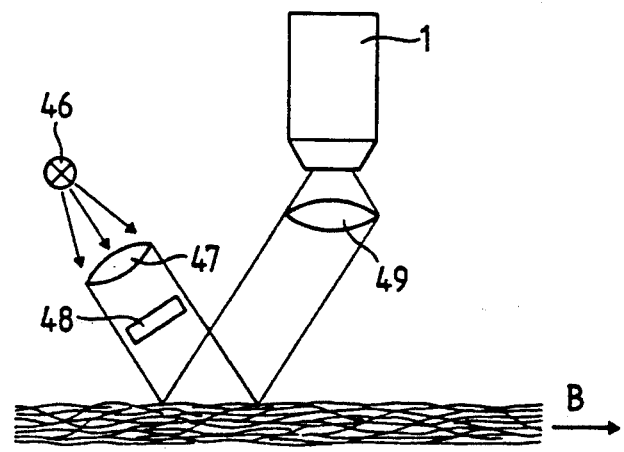
FIG. 4d

METHOD AND APPARATUS FOR MEASURING THE NATURAL COLOR OF SLIVERS

BACKGROUND OF THE INVENTION

1. Field of the Invention

The present invention relates to the field of textile technology and, more particularly, relates to a method and an apparatus for in-line color measurement of slivers.

2. Description of Background and Other Information

Color measurement of various materials is a widely used technique. Thus, color sensors for a large number of applications are to be found on the market. They may be used for laboratory methods and for in-line methods of process monitoring and control. Such color measurements do not generally cause significant problems where compact materials with smooth surfaces are concerned. However, for loose materials (e.g., powder), strongly porous materials (e.g., sintering bodies), a standardized preparation of the samples is required. Therefore, materials like cotton wool, for example, only provide reproducible and meaningful color measurement results if such materials are brought to the color sensor in a form which is as standardized as possible. In the field of textile technology, such standardized color measurements are also performed on stationary samples of fiber material.

In the various stages of textile production, color measurements are performed and the measured data are then utilized for process monitoring and control. In the area of the preparatory machine, the in-line color measurement of slivers, in particular, would be preferable. However, such measurements have not yet been performed or perfected due to the fact that, presently, no method is known with which one could perform the manipulation in continuously moving slivers, which is necessary for the standardized sample preparation, without permanently changing the slivers or disturbing the process. A permanent change in the sliver to be measured is, under all circumstances, not acceptable, neither with regard to the sliver's mass per unit of length, its density, the orientation of the slivers, nor its randomly laid layer.

SUMMARY OF THE INVENTION

It is therefore an object of the present invention to propose a method and to create an apparatus by means of which it is possible to direct the continuously moving sliver to be measured, the sliver being conditioned as to allow the measurement of the color, past the measuring point so that the color of the sliver may be measured by a commercially available color sensor. Such measurement is to provide reproducible and precise measured data. Any optional conditioning of the sliver for the measurement must not adversely influence the process of the sliver. Even after the sliver has passed the measuring point, it must fulfill all requirements of the process concerning the parameters of its properties. In particular, the measuring process must not slow down the advancement of the sliver, as that would lead to a subsequent stretching of the fiber arrangement in the sliver. The measuring apparatuses are to be disposed in or built into existing processing apparatuses for producing, conveying or processing slivers in such a manner that the operation of the respective processing apparatuses is not disturbed.

In order to bring about meaningful and reproducible measured values in in-line color measurements of continuously moving slivers, it is necessary to compress the slivers when they pass the measuring point at which the color measurement is performed by means of a commercially available color measuring device. In accordance with the method of the invention, a point in the process is selected as a measuring point at which the sliver is compressed within said process and comprises a sufficient layer thickness.

Possible procedures for color measurement during the manufacturing process and some embodiments of auxiliary measurement apparatuses arranged in accordance with the invention are hereinafter more particularly described.

Accordingly, the present invention includes a method and apparatus for in-line color measurement of continuously moving fiber material, during a fiber material process, by using a color measuring device.

This apparatus of the invention is capable of performing the method including the steps of: compressing the continuously moving fiber material at a processing position; illuminating the fiber material at the processing position by means of a light probe provided at the processing position, thereby defining a measuring position; detecting light reflected transversely of a direction of movement of the fiber material; and evaluating the reflected light for obtaining a color measurement of the continuously moving fiber material; wherein the processing of the fiber material is substantially not affected by the steps of illuminating, detecting, and evaluating.

In one embodiment of the present invention, the measuring position is selected at a point in the fiber material process at which the fiber material is coiled in overlapping layers in a sliver coiler, and the fiber material is monitored at a processing position includes a measuring opening in an upper part of the sliver coiler.

In a particular aspect of the invention, the measuring position is located at a sliver coiler into which the fiber material is directed, the sliver coiler having an upper part, and the surface of the sliver being pressed against the upper part of the sliver coiler is measured during movement of the fiber material.

In another embodiment of the present invention, the fiber material is advanced through a hopper having a mouth through which the fiber material advances, the means for enabling the monitoring of the fiber material at a processing position being arranged in the hopper. In this embodiment, the means for detecting and evaluating include a measuring probe arranged generally perpendicular to the mouth. The hopper has a cross-section having a general shape of a rectangle and the hopper further has a wall facing the measuring probe, the wall having a transparent portion, the hopper having a wall opposite the transparent portion provided with a calibration color.

According to a further preferred embodiment of the invention, the illumination of the material is achieved by means of a color measuring instrument having a xenon flash lamp; the detection step of the invention includes detecting light generally perpendicularly incident to the fiber material; and the step of evaluating is performed by the color measuring instrument having a measuring circuit for automatically compensating deviations in the internal lighting equipment.

Further according to the present invention, the measuring instrument is periodically calibrated with a calibration color.

In a further aspect, the method includes adjusting the calibration color to the material and the color of the fiber material being measured. It is contemplated that the measuring calibration can be performed by positioning the calibration color beneath the light probe, the light probe being stationary or, alternatively, by positioning the light probe over the calibration color.

In another aspect of the invention, the measuring probe is either continuously or periodically cleaning. Various means can be employed for performing the cleaning, such as the provision of an ejected air stream or a mechanical cleaning element such as a brush, for example.

It is contemplated that either or both the calibration and cleaning can be performed automatically as part of a predetermined process, e.g., at predetermined intervals.

Still further, deviations in illumination intensity or temperature can be monitored and the step of calibrating can be performed as a function thereof.

It is also contemplated, according to the present invention, to perform an auxiliary measurement to counter variations of light intensity in the fiber material to be measured and that, for measurement at the same degree of light intensity, an auxiliary measurement is performed, whereby the measurement is used for controlling the measuring process. The auxiliary measurement can consist of measuring the density of the fiber material and the color measurement is initiated at a predetermined degree of density. The auxiliary sensor includes a fiber density measuring sensor, and the auxiliary sensor is arranged, in a direction in which the fiber material is advanced, in an upstream position with respect to the means for detecting and evaluating.

In a particular aspect of the invention, it is contemplated that before each step of calibrating the measuring instrument, a cleaning of the light probe is performed.

It is a further object of the invention to perform the steps of illuminating, detecting, and evaluating at at least two can coilers and processing data obtained by the step of evaluating for a series of measurements.

In an efficient embodiment of the invention, the step of compressing the continuously moving fiber material includes a process-inherent compression of the fiber material, i.e., an additional, independent compression of the fiber material is unnecessary.

BRIEF DESCRIPTION OF THE DRAWINGS

The above and additional objects, characteristics, and advantages of the present invention will become apparent in the following detailed description of preferred embodiments with reference to the accompanying drawings which are presented as non-limiting examples, in which:

FIGS. 4a–4d illustrate embodiments for auxiliary apparatuses for cleaning and calibrating the color measurement sensor or the auxiliary measuring apparatuses;

DETAILED DESCRIPTION OF PREFERRED EMBODIMENTS

Figure 1A:
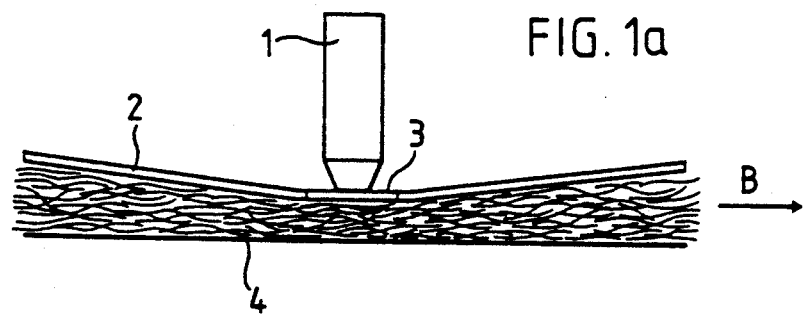
FIGS. 1a to 1d illustrate possible variations of the methods in a schematic representation.

Color measurements of stationary samples of slivers have shown that reproducible measured values are only achieved if the slivers are compressed, for example, to a standardized degree of compression, and if the slivers or the fibers contained in the slivers always have the same orientation with regard to the measuring instrument. The measurements are precise and reproducible if the measuring probe is kept dustfree and is calibrated with a calibration color suitable for the material or the color to be measured. Suitable color measuring devices known in the art are, for example, the Minolta Chroma-Meter, in particular the CR-200 and CR-210 types. They are color measuring devices which comprise a xenon flash light for diffuse lighting of the sample surface, a measuring system which only evaluates light which is vertically incident to the surface of the sample, and an electronic measuring system which automatically compensates deviations in the lighting of the measurement. The measuring principles of such color measuring devices and the interpretation of the measured results are to be found in the pertinent literature relating, e.g., to the aforementioned measuring devices.

The procedure discussed hereinafter (see FIG. 1a) transmits the results obtained from the stationary samples to the continuously moving slivers. For continuous color measurement, the same color measuring devices are preferably used which are also used for the stationary color measurement. This then requires the measuring process to be altered, which is the subject matter of the present invention.

In the drawings, a sufficient portion of sliver processing apparatus, and the sliver extending in association therewith, is shown to permit those of ordinary skill in the art to make and use the present invention. Any details not illustrated are only omitted for the sake of clarity in the presentation of the present invention.

With initial reference to FIG. 1a, a measuring probe 1 is disposed vertically, or generally vertically, to the sliver's direction of feed B, and the surface of the sliver moves past said probe at a constant distance therefrom. As long as the position of the fibers in the sliver remain constant, the condition of constant orientation of the fibers continues to be fulfilled. Before the sliver moves past the measuring point, it is slightly compressed by a compressing means 2, shown in the drawing as a restricted guide means for the sliver. The color measurement is made through a component 3 of the apparatus, the component being transparently arranged to have a transparent portion (e.g., a transparent face plate) or a small opening (without a face plate) between the compressing means, whereby the opening is dimensioned in accordance with the fiber length, so small that the sliver does not expand into the opening during its movement past the opening. By providing a pertinent arrangement of the compressing means, either as a consequence of the process or of the measurement itself, it is ensured that at the measuring point the sliver is wide enough to cover the whole opening of the color measuring probe. The less optical interfaces provided in the path of the rays of the illumination and measuring light, the more precise the color measurement will become.

For compressing the sliver in the area of the measuring point, there are several methods available which are known to those skilled in the art. For example, Swiss Patent Application No. 00 786/90-5, filed on Mar. 12, 1990, the priority of which is claimed for the instant application, and the disclosure of which is hereby incorporated by reference thereto, in its entirety, extensively describes several variations for continuous color measurement of slivers. In accordance with a procedure pursuant to FIG. 1b, the measurement is made at a point in the process at which the sliver is already compressed as a part of the process, i.e., the compressing means 2b, e.g., a sliver funnel, constitutes an inherent part of the process. In accordance with a procedure pursuant to FIG. 1c, the measurement is made in any desirable processing section and the sliver is compressed without deceleration in the area of the measuring point or between the compressing means 2c extending along with the sliver. In accordance with a procedure pursuant to FIG. 1d, the measurement is performed at a processing point at which the sliver sags so that it may be briefly stopped for the measurement and compressed between the stationary compressing means 2d.

In accordance with a preferred embodiment, the measurement is performed at a processing point at which the sliver is compressed within the process, i.e., where the compressing means, a sliver coiler device, for example, constitutes a component inherent to the process.

As in most cases, the sliver is not absolutely compact and opaque in the compressed condition, the color of the background, i.e., area 4 which is opposed to the measuring probe on the other side of the sliver, influences a part of the reflected light and, thus, the measurement of the color. The most preferable color for the background surface depends upon the material to be measured. In most cases a defined "white" has proved to be a preferable background color. The measured values of the color measurement may then be subjected to a material-dependent correction which compensates, depending upon the sliver's "transparency" and other sliver properties (the material of which the sliver is comprised, or the sliver cross-section, e.g.), the influence of the background color on the measurement. In one of the procedures proposed hereinafter, the influence of the background effect and the thus resulting countermeasures for elimination of such background effect by way of measurement techniques is elegantly avoided. In this embodiment, a measuring point is used in a processing section in which the maximum measuring depth is encompassed by the sliver to be measured and, thus, no compensation for color reflection is required to be made.

Before and during the measurement, the measuring instrument is calibrated. For example, a surface comprising a certain calibration color is periodically measured. The calibration color is to be selected in accordance with the sliver material, whereby, as a rule, a defined "white" may also be used. The calibration is performed by bringing together the calibration area with the measuring area of the measuring probe, e.g., by moving the measuring probe back and forth over the calibration area, or vice-versa, or by moving the calibration area back and forth under the measuring probe or by optical projection of a respective color patch in the area of the measuring probe.

The number of calibrations to be performed depends upon the requirements which the color measurement has to fulfill. In cases with low requirements, it is sufficient to manually perform the calibration off-line in stationary or maintenance periods. For higher requirements, the calibration must be performed more often, preferably automatically. Said calibration may be performed either in accordance with a timed schedule, i.e., after certain predetermined periods (hours, days, weeks), or controlled, i.e., in accordance with other predetermined measuring criteria (e.g., a change in the power of the probe's light, deviations in the surrounding temperature).

Figure 1B:
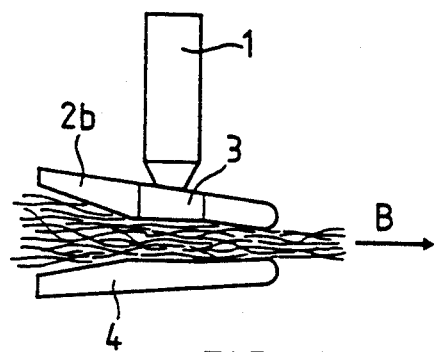
Figure 1C:
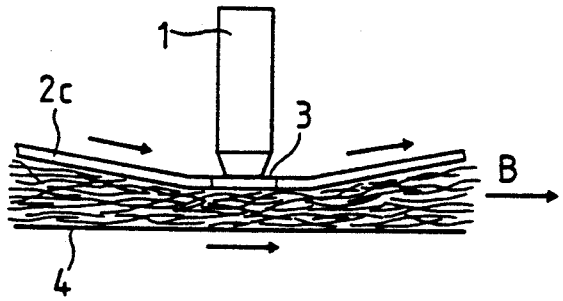
Figure 1D:
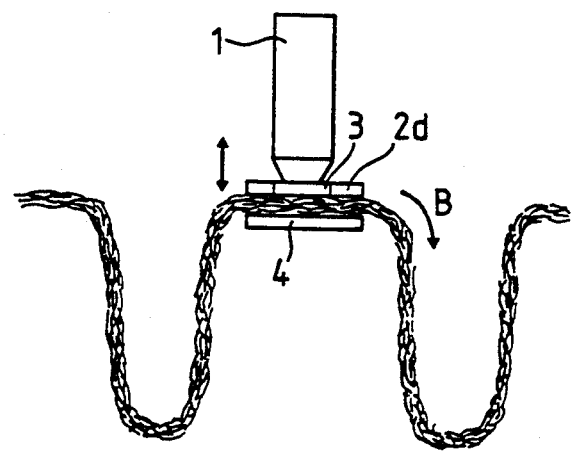
Figure 2:
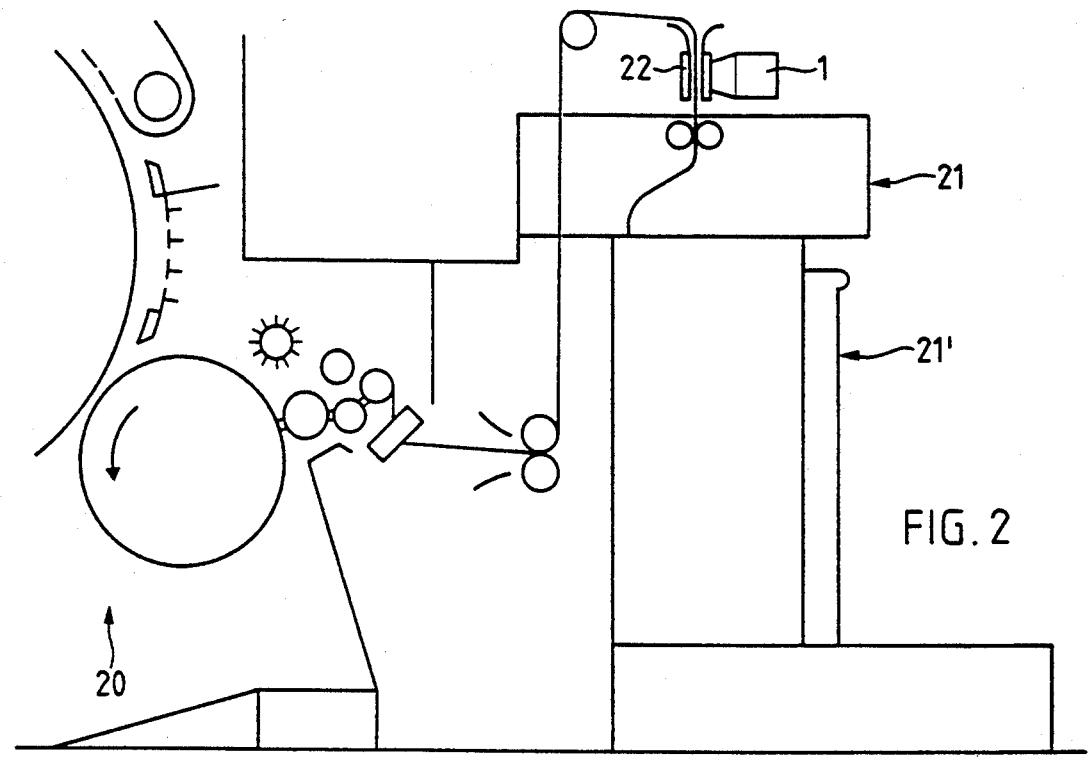
FIG. 2 illustrates an option for conditioning the sliver to be measured which makes use of fiber compression caused by the process.
Figure 3A:
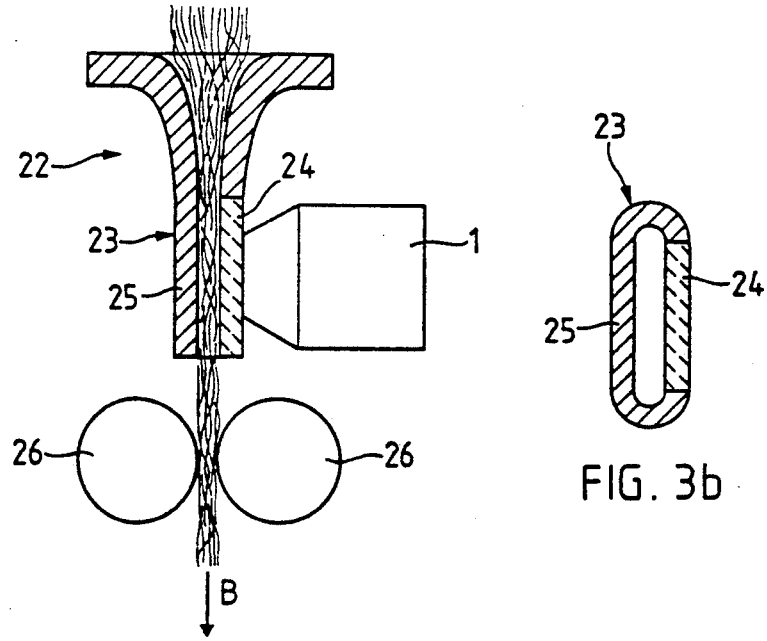
FIGS. 3a and 3b illustrate details of an auxiliary measuring apparatus for realizing the color measurement, as is shown in FIG. 2.
Figure 3B:
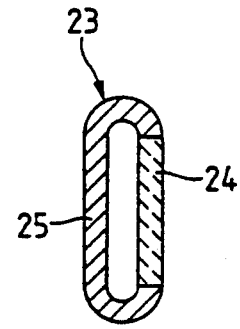

FIG. 2 shows a measuring point in the sliver coiler having a first point at which the compressing of the sliver takes place, said compressing being inherent to the process. For the purpose of compressing the sliver use is made of a feed hopper, i.e., a variation of the method pursuant to FIG. 1b is applied. It shows the output of a sliver from a carding machine 20 and its delivery to a sliver coiler device 21 on can 21'. Measuring probe 1 is installed on hopper 22 of the sliver coiler. As can be seen in FIG. 3a, hopper 22 is specially designed for this purpose. The hopper mouth 23 is arranged as a measuring cell. In order to provide the sliver with sufficient width for the color measurement, hopper mouth 23 is generally shaped like a rectangle with rounded edges, as is shown in the cross-section in FIG. 3b. The wide side 24 of hopper mouth 23, the side facing towards the measuring probe 1, consists of a transparent material. The opposite side 25 carries an exchangeable or replaceable surface with the suitable background color facing towards the sliver. Such replaceable surface could take the form, e.g., of a layer of a suitably colored material to be removably affixed to side 25, or a portion of side 25 immediately opposite the transparent material on side 24 could itself be removably attached to the remainder of the hopper. Access to the replaceable surface on side 25 could be gained by means of the transparent material on side 24 itself being removable. A pair of conveying rollers 26 follows the feed hopper in the direction B of the sliver's movement.

Although the compression inherent to the process is utilized in this method, the measuring depth, however, is still within the critical range in which the influence of the background color is still present. A further method with a measuring point at which a second process-inherent compression occurs is described hereinafter. Said method is also resistant against the influence of the background color.

FIGS. 4a-4d show some embodiments by way of example concerning parts of the apparatus which serve for calibrating and cleaning the color measuring probe. FIG. 4a shows a swivelling fixing device 40 for a measuring probe 1 which allows, for manual or automatic cleaning or calibration, moving the measuring probe from its measuring position (horizontal swing in accordance with arrow a) via a mechanical cleaning element 41, for example a brush, and (horizontal swing in accordance with arrow b) subsequently via a calibration area 42 and (horizontal swing in accordance with arrow c) back to the measuring point again. A respectively combined cleaning and calibration process may be performed sufficiently fast by automated driving means so that the series of in-line color measurements need not be interrupted.

FIG. 4b shows a device for continuous cleaning of the measuring probe 1. From a respectively arranged nozzle 43 a continuous flow of air 44 is blown between measuring probe 1 and the sliver, or between the measuring probe 1 and the transparent plate 43. This measure ensures that no dust settles in the measuring probe, which would otherwise adversely affect said measurements.

FIG. 4c shows an example of a mechanical arrangement for cleaning the opening of the measuring probe. A slender brush 45 is either manually or automatically swivelled across the opening of measuring probe 1.

FIG. 4d shows the arrangement of an apparatus by which the image of a color patch is to be projected onto the moving sliver for calibration purposes. A light source 46 is displayed on the sliver as a patch of color by means of lens 47. This is achieved in that either the light source emits colored light or the lens is provided with a color filter. The patch of color is either projected onto the point at which the color of the sliver is measured by measuring probe 1 or it is displayed, by means of additional optical devices, e.g., lens 49, in the opening of measuring probe 1. A gloss trap 48 prevents that the calibration image from being adversely affected by reflected light. Said apparatus may simultaneously be used for illuminating the sliver.

Figure 5:
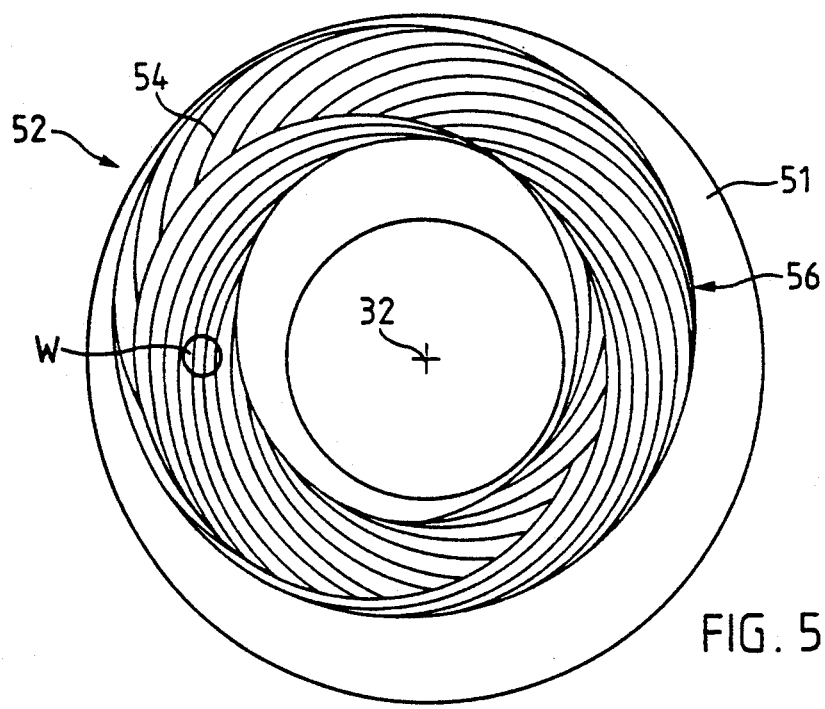
FIG. 5 illustrates another preferable measuring point in the same area of the processing of the sliver (sliver coiler or can coiler, e.g.) in which the sliver to be measured is subjected to compression caused by the process.

FIG. 5 schematically shows another preferable measuring point in the area of the sliver coiler, whereby the area comprises a processing stage which is particularly suitable for the measurement of slivers. In the can coiler, the sliver is spirally coiled and compressed between the can bottom and the upper part of the sliver coiler to form an equalized "sliver cake", the "cake" constituting a certain form of continuous coiling of the sliver. The compression is performed in that a moveable can bottom presses the sliver against the upper part from below, whereby simultaneously the sliver is continuously introduced between the sliver cake and the upper part of the sliver coiler. A relative movement takes place between the surface of the sliver cake, which is continuously newly formed, and the upper part of the sliver coiler. The sliver cake turns around the can axis and, during the coiling of the sliver, new sliver material is continuously moved past the upper part of the sliver coiler. From a processing point of view, the measuring conditions are preferable.

If an auxiliary measuring device, e.g., a measuring opening W through which the sliver pressed against the upper part of the sliver coiler may be illuminated and measured, is arranged in the upper part of the sliver coiler, it would be possible to measure, without any interruption of the process, the sliver which continuously prepares and renews itself for the measurement. The continuously coiled sliver is moved past the sensor shortly after the coiling thereof and may thus be measured by the sensor. The measuring window interfacing with the sliver is self-cleaning and, on the side of the sensor, one of the above-mentioned cleaning and calibration devices discussed in context with FIGS. 4a–4d may be disposed. Thus, the dust is removed from the measuring opening either continuously by directing a flow of air past the opening or discontinuously by providing a mechanical cleaning tool, e.g., a brush. The discontinuous mechanical cleaning of the opening as well as the calibration may be performed either off-line or manually, or controlled and regulated automatically. The advantage of this measuring area is, on the one hand, due to the fact that the sliver is "opaque", i.e., the thickness and the density of the lamination is so high that the background effects cease to have any effect, and that the fibers of the sliver are stored (after the carding machine) in a cleaned, equalized (parallelized) condition and in a regular arrangement (as sliver cake), thus avoiding temporarily disturbing influences in the measurement.

Note must be taken of the fact that the sliver must not be moved past the sensor in the direction of its natural longitudinal orientation which could lead to deviations in brightness. This influence can be counteracted by using an auxiliary sensor, for instance a capacitative sensor, which is arranged, in the direction of the processing, in front, said sensor allowing the determination of the sliver density. Said sensor would trigger the color measuring sensor for the measuring process.

The preferred measuring position in the process is located, as was mentioned above, on the sliver coiler, more precisely on the upper part of the coiler. FIG. 5 shows a specific monitoring point for the sliver, said monitoring point being adjusted to the process and being provided in form of an opening, schematically represented as a circle W, which is suitable for the color measurement of the proposed kind. A can 52 comprises on the can bottom 51 a sliver cake layer 56 of sliver 54. The layer eccentrically laid around the can's center of rotation 32 is covered by further layers when the can is filled, said further layers being eccentrically displaced with regard to the direction of rotation, so that the can bottom is fully covered after a few layers of sliver cake. Commonly, this process requires less than one minute of filling time. The surface of the stack of sliver cake consists of a macroscopically complex arrangement of sliver flow which, when seen through the measuring opening, shows the same flow due to their overall movement around the center of rotation and which are conditioned for the measurement by the process-inherent pressure of the sliver cake layers against the upper part of the sliver coiler.

Figure 6A:
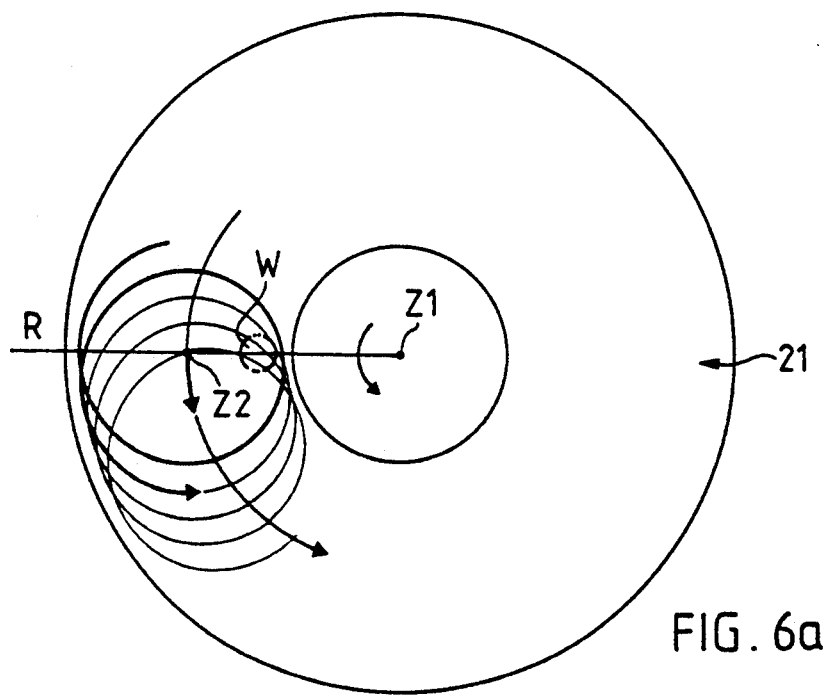
FIGS. 6a and 6b illustrate a measuring arrangement in the measuring point as shown in FIG. 5.
Figure 6B:
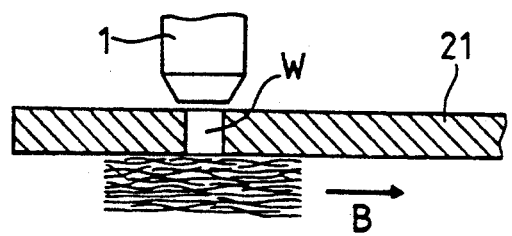

FIGS. 6a and 6b shows another mode of coiling the slivers which is inherent to the process. The sliver lap is laid around a first and second center of rotation Z1, Z2, respectively, in such a manner that the slivers are arranged spirally around a center. Here the slivers are also pressed by the can bottom against the upper part of the sliver coiler.

As is shown in FIG. 6a, a measuring opening W is arranged in the upper part of sliver coiler 21. The uppermost sliver layer B is pressed against said upper part and moved past said opening W (see FIG. 6b). As was already mentioned above, said opening may, for example, be closed by a face plate or be open (whereby the edges of the holes on the side of the sliver are rounded off accordingly). Such an opening, if circular, comprises a diameter of 5 to 10 millimeters (mm) so that both options may be taken into account: the minimization of optical interfaces by leaving out a face plate or by increasing the opening which normally requires a face plate to be used. It is also possible to use non-plane optical means such as focusing lenses. Such means are described in the Swiss Patent Application No. 00 786/90-5.

In the radial direction to the can's center of rotation the position of the opening may be selected in such a way that the structure of the compressed sliver moving below the measuring opening is to be as fine as possible which usually is the case on the inner edge of the pressed sliver cake. In such a manner, the measuring position may be optimized.

In normal operation, the color values of the card sliver are measured at certain intervals, e.g., 10 seconds. The change of a can interrupts the color measurement for approximately 5%-10% of the time required for filling the can. This constitutes a blind phase in the measuring process or a measuring gap, respectively. The measuring gap, in which no color data are obtained, may be reduced or avoided in that further color sensors, are used in can coilers for card slivers of the same type, said can coilers running parallel. If the change of cans is timed in such a manner that during the change color data are gained from at least one of the sensors it is possible to measure continuously the color of the sliver. It is nearly impossible that all cans are changed at once, even more so if organizational measures are set with regard to the timing of the change of the cans.

The use of a second sensor in the adjoining sliver coiler alone will contribute to avoiding disturbances when changing a can. The probability that both sliver coilers change their cans simultaneously is negligibly low. A second measuring point (or several such points) has further advantages, i.e., redundancy by twice as many measurements in the event that the measurements take place simultaneously (only during the short period of changing the can there is no redundancy).

In addition to the aforementioned Swiss Patent Application No. 00786/90-5, Applicants also hereby incorporate by reference thereto, in its entirety, Swiss Patent Application No. 01 319/90-1, filed on Apr. 19, 1990, the priority of which is claimed for the instant application.

Finally, although the invention has been described with reference of particular means, materials and embodiments, it is to be understood that the invention is not limited to the particulars disclosed and extends to all equivalents within the scope of the claims.

What is claimed is:

1. A method for in-line color measurement of continuously moving fiber material, during a fiber material process, by using a color measuring device, said method comprising the steps of:
   compressing the continuously moving fiber material at a processing position;
   illuminating the fiber material at the processing position by means of a light probe provided at the processing position, thereby defining a measuring position;
   detecting light reflected transversely of a direction of movement of the fiber material; and
   evaluating the reflected light for obtaining a color measurement of said continuously moving fiber material;
   wherein the processing of the fiber material is substantially not affected by said steps of illuminating, detecting, and evaluating, and wherein the fiber material comprises a carding sliver band, and wherein:
   said measuring position is selected at a point in the fiber material process between the outlet of a card and the inside of a sliver coiler in which the fiber material is coiled in overlapping layers.

2. The method as defined in claim 1, wherein:
   said measuring position is selected at a point in the fiber material process at which the fiber material is coiled in overlapping layers.

3. The method as defined in claim 1, wherein:
   said measuring position is located at a sliver coiler into which said fiber material is directed, said sliver coiler having an upper part, and the surface of the sliver being pressed against the upper part of the sliver coiler is measured during movement of said fiber material.

4. The method as defined in claim 1, wherein:
   said step of illuminating is performed by means of a color measuring instrument having a xenon flash lamp;
   said step of detecting includes detecting light generally perpendicularly incident to the fiber material; and
   said step of evaluating is performed by the color measuring instrument having a measuring circuit for automatically compensating deviations in the internal lighting equipment.

5. The method as defined in claim 4, further comprising the step of:
   periodically calibrating the measuring instrument with a calibration color.

6. The method as defined in claim 5, further comprising:
   adjusting the calibration color to the material and the color of the fiber material being measured.

7. The method as defined in claim 5, wherein:
   the step of periodically calibrating the measuring instrument is performed by positioning the calibration color beneath the light probe, the light probe being stationary.

8. The method as defined in claim 5, wherein:
   the step of periodically calibrating the measuring instrument is performed by positioning the light probe over the calibration color.

9. The method as defined in claim 5, wherein:
   the step of periodically calibrating the measuring instrument is performed by optically projecting the calibration color into an area of the light probe, the light probe being stationary.

10. The method as defined in claim 5, further comprising the step of:
    detecting deviations in illumination intensity and performing said step of calibrating the measuring instrument as a function of the detected deviations in illumination intensity.

11. The method as defined in claim 5, further comprising the step of:
    detecting deviations in the temperature and performing said step of calibrating the measuring instrument as a function of the detected deviations in temperature.

12. The method as defined in claim 5, wherein:
    before each step of calibrating the measuring instrument, a cleaning of the light probe is performed.

13. The method as defined in claim 1, further comprising the step of:
    cleaning the light probe.

14. The method as defined in claim 13, wherein:
    said step of cleaning comprises continuously cleaning the light probe.

15. The method as defined in claim 13, wherein:
    said step of cleaning comprises periodically cleaning the light probe.

16. The method as defined in claim 13, wherein:
    said step of cleaning comprises ejecting an air stream toward light probe.

17. The method as defined in claim 13, wherein:
    said step of cleaning comprises utilizing a mechanical cleaning means.

18. The method as defined in claim 17, wherein:

said step of cleaning comprises moving a mechanical cleaning element over an opening of the light probe.

19. The method as defined in claim 17, wherein:
said step of cleaning comprises moving the light probe over a mechanical cleaning element.

20. The method as defined in claim 17, wherein:
said step of cleaning comprises utilizing a brush.

21. The method as defined in claim 13, further comprising the step of:
automatically controlling the step of periodically calibrating.

22. The method as defined in claim 13, further comprising the step of:
automatically controlling the step of cleaning the light probe.

23. The method as defined in claim 1, further comprising the step of:
performing an auxiliary measurement to counter variations of light intensity in the fiber material to be measured and that, for measurement at the same degree of light intensity, an auxiliary measurement is performed, whereby said measurement is used for controlling the measuring process.

24. The method as defined in claim 23, wherein:
the auxiliary measurement consists of measuring the density of the fiber material and the color measurement is initiated at a predetermined degree of density.

25. The method as defined in claim 1, further comprising:
performing said steps of illuminating, detecting, and evaluating at least two can coilers; and
processing data obtained by said step of evaluating for a series of measurements.

26. The method as defined in claim 1, wherein:
said step of compressing said continuously moving fiber material comprises a process-inherent compression of the fiber material.

27. An apparatus for preparing the in-line color measurement of fiber material during an in-line fiber material process, the fiber material process including at least a card and a sliver coiler, said apparatus comprising:
means for enabling the monitoring of the fiber material at a processing position at which the fiber material is compressed and advanced, said processing position being a point in the fiber material process between an outlet of the card and inside of the sliver coiler in which the fiber material is coiled in overlapping layers;
means for projecting light in a predeterminate direction through said means for enabling the monitoring of the fiber material; and
means for detecting and evaluating light reflected by said fiber material in a further direction opposite of said predeterminate direction through said means for enabling the monitoring of the fiber material at said processing position.

28. The apparatus as defined in claim 27, further comprising:
means for compressing said fiber material at said processing position.

29. The apparatus as defined in claim 28, wherein:
said means for compressing said fiber material is process-inherent.

30. The apparatus as defined in claim 27, wherein
said means for enabling the monitoring of the fiber material at a processing position comprises a measuring openinging an upper part of the sliver coiler.

31. The apparatus as defined in claim 30, wherein:
said measuring opening is closed by a transparent face plate.

32. The apparatus as defined in claim 27, further comprising:
a hopper having a mouth through which said fiber material advances, said means for enabling the monitoring of the fiber material at a processing position being arranged in said hopper;
said means for detecting and evaluating comprising a measuring probe arranged generally perpendicular to said mouth, said hopper having a cross-section having a general shape of a rectangle, said hopper further having a wall facing said measuring probe, said wall having a transparent portion, said hopper having a wall opposite said transparent portion provided with a calibration color.

33. The apparatus as defined in claim 32, wherein:
said opposite wall comprising means for replacing said calibration color.

34. The apparatus as defined in claim 33, further comprising:
a light guide positioned between said fiber material being advanced and said means for detecting and evaluating.

35. The apparatus as defined in claim 27, further comprising:
a swivelling carrier, said means for detecting and evaluating being arranged on said swivelling carrier for moving in a swivelling area; and
said apparatus further comprising a calibration means and a cleaning means in said swivelling area of said means for detecting and measuring.

36. The apparatus as defined in claim 27, further comprising:
an air nozzle arranged in such a manner that the means for enabling the monitoring of the fiber material at a processing position further comprises means for continuously subjecting said processing position to a flow of air.

37. The apparatus as defined in claim 27, further comprising:
an auxiliary sensor comprising means for influencing said for detecting and evaluating.

38. The apparatus as defined in claim 37, wherein:
said auxiliary sensor comprises a fiber density measuring sensor, and wherein said auxiliary sensor is arranged, in a direction in which the fiber material is advanced, in an upstream position with respect to said means for detecting and evaluating.

39. An apparatus at a carding line, as defined in claim 27, comprising:
at least two can coilers, each of said can coilers having a respective means for enabling monitoring of the fiber material at a processing position; means for projecting light; and means for detecting and evaluating light;
said apparatus further comprising means for combining detected and evaluated data at said at least two processing positions.

* * * * *